(12) United States Patent
Jennings

(10) Patent No.: US 7,566,791 B2
(45) Date of Patent: *Jul. 28, 2009

(54) SUBSTITUTED 3-CARBONYL-1H-INDOL-1YL ACETIC ACID DERIVATIVES AS INHIBITORS OF PLASMINOGEN ACTIVATOR INHIBITOR-1 (PAI-1)

(75) Inventor: Lee D. Jennings, Chestnut Ridge, NY (US)

(73) Assignee: Wyeth, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/375,954

(22) Filed: Mar. 15, 2006

(65) Prior Publication Data

US 2006/0178412 A1 Aug. 10, 2006

Related U.S. Application Data

(62) Division of application No. 10/731,723, filed on Dec. 9, 2003, now Pat. No. 7,078,429.

(60) Provisional application No. 60/432,107, filed on Dec. 10, 2002.

(51) Int. Cl.
*C07D 209/12* (2006.01)
*A61K 31/405* (2006.01)

(52) U.S. Cl. ..................... 548/493; 514/414

(58) Field of Classification Search ............. 548/493; 549/58
See application file for complete search history.

(56) References Cited

U.S. PATENT DOCUMENTS

| | | | | |
|---|---|---|---|---|
| 3,026,325 A | 3/1962 | Heinzelman et al. | ........ | 548/496 |
| 3,476,770 A | 11/1969 | Scherrer | ........ | 548/494 |
| 3,557,142 A | 1/1971 | Bell | ........ | 548/516 |
| 3,843,683 A * | 10/1974 | Bell | ........ | 548/493 |
| 4,478,819 A | 10/1984 | Hercelin et al. | ........ | 424/457 |
| 4,736,043 A | 4/1988 | Michel et al. | ........ | 548/492 |
| 4,851,406 A | 7/1989 | Martens et al. | ........ | 514/217.04 |
| 5,164,372 A | 11/1992 | Matsuo et al. | ........ | 514/19 |
| 5,420,289 A | 5/1995 | Musser et al. | ........ | 548/159 |
| 5,482,960 A | 1/1996 | Berryman | ........ | 514/414 |
| 5,502,187 A | 3/1996 | Ayer et al. | ........ | 544/117 |
| 5,541,343 A | 7/1996 | Himmelsbach et al. | ........ | 514/424 |
| 5,612,360 A | 3/1997 | Boyd et al. | ........ | 514/381 |
| 5,859,044 A | 1/1999 | Dow et al. | ........ | 514/419 |
| 6,048,875 A | 4/2000 | De Nanteuil et al. | ........ | 514/314 |
| 6,110,963 A | 8/2000 | Malamas | ........ | 514/443 |
| 6,166,069 A | 12/2000 | Malamas et al. | ........ | 514/469 |
| 6,232,322 B1 | 5/2001 | Malamas et al. | ........ | 514/303 |
| 6,251,936 B1 | 6/2001 | Wrobel et al. | ........ | 514/443 |
| 6,302,837 B1 | 10/2001 | De Nanteuil et al. | ........ | 514/337 |
| 6,479,524 B1 | 11/2002 | Priepke et al. | ........ | 514/352 |
| 6,599,929 B2 | 7/2003 | Cho et al. | ........ | 514/415 |
| 6,787,556 B1 | 9/2004 | Hargreaves et al. | ........ | 514/311 |
| 6,800,645 B1 | 10/2004 | Cox et al. | ........ | 514/314 |
| 6,800,654 B2 | 10/2004 | Mayer et al. | ........ | 514/381 |
| 6,844,358 B2 | 1/2005 | Malamas et al. | ........ | 514/336 |
| 7,078,429 B2 * | 7/2006 | Jennings | ........ | 514/419 |
| 2003/0013732 A1 | 1/2003 | Elokdah | ........ | 514/301 |
| 2003/0018067 A1 | 1/2003 | Elokdah et al. | ........ | 514/469 |
| 2003/0060497 A1 | 3/2003 | Gerlach | ........ | 514/414 |
| 2003/0125371 A1 | 7/2003 | Elokdah et al. | ........ | 514/419 |
| 2004/0116488 A1 | 6/2004 | Jennings et al. | ........ | 514/374 |
| 2004/0116504 A1 | 6/2004 | Elokdah et al. | ........ | 514/419 |
| 2004/0138283 A1 | 7/2004 | Jennings et al. | ........ | 514/414 |
| 2004/0204417 A1 | 10/2004 | Perez et al. | ........ | 514/249 |
| 2005/0070584 A1 | 3/2005 | Havran et al. | ........ | 514/357 |
| 2005/0070585 A1 | 3/2005 | Elokdah et al. | ........ | 514/364 |
| 2005/0070587 A1 | 3/2005 | Elokdah et al. | ........ | 514/381 |
| 2005/0070592 A1 | 3/2005 | Gundersen | ........ | 514/415 |
| 2005/0096377 A1 | 5/2005 | Hu | ........ | 514/419 |
| 2005/0113428 A1 | 5/2005 | Gopalsamy et al. | ........ | 514/364 |
| 2005/0113436 A1 | 5/2005 | Elokdah et al. | ........ | 514/411 |
| 2005/0113438 A1 | 5/2005 | Hu et al. | ........ | 514/414 |
| 2005/0113439 A1 | 5/2005 | Hu | ........ | 514/414 |
| 2005/0119296 A1 | 6/2005 | Elokdah et al. | ........ | 514/300 |
| 2005/0119326 A1 | 6/2005 | Havran et al. | ........ | 514/414 |
| 2005/0119327 A1 | 6/2005 | Hu | ........ | 514/414 |
| 2005/0215626 A1 | 9/2005 | Havran et al. | ........ | 514/469 |
| 2006/0020003 A1 | 1/2006 | Commons et al. | ........ | 514/419 |
| 2006/0052348 A1 | 3/2006 | Commons et al. | ........ | 514/92 |
| 2006/0052349 A1 | 3/2006 | Commons et al. | ........ | 514/95 |
| 2006/0052420 A1 | 3/2006 | Commons | ........ | 514/340 |

FOREIGN PATENT DOCUMENTS

DE 3147276 A1 6/1983

(Continued)

OTHER PUBLICATIONS

Cancer and Metastasis Reviews (1998),17(1), 91-106.*

(Continued)

*Primary Examiner*—Rebecca L Anderson
*Assistant Examiner*—Shawquia Young
(74) *Attorney, Agent, or Firm*—Mabel Ng; Scott Larsen; David Kurlandsky

(57) ABSTRACT

Substituted 3-carbonyl-1H-indol-1-yl acetic acid derivatives of formula I are provided:

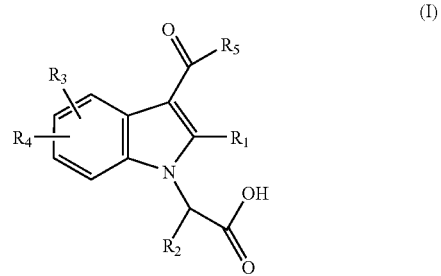

(I)

wherein: $R_1$, $R_2$, $R_3$, $R_4$ and $R_5$ are as defined herein which are useful as inhibitors of plasminogen activator inhibitor-1 (PAI-1) for treating conditions resulting from fibrinolytic disorders, such as deep vein thrombosis and coronary heart disease, and pulmonary fibrosis.

19 Claims, No Drawings

FOREIGN PATENT DOCUMENTS

| | | |
|---|---|---|
| DE | 43 38 770 A1 | 5/1995 |
| DE | 19543639 A1 | 5/1997 |
| DE | 19753522 | 6/1999 |
| EP | 0 416 609 A2 | 3/1991 |
| EP | 0 508 723 A1 | 10/1992 |
| EP | 0 512 570 A1 | 11/1992 |
| EP | 0 540 956 A1 | 5/1993 |
| EP | 0 655 439 A2 | 5/1995 |
| EP | 0 759 434 A1 | 2/1997 |
| EP | 0 819 686 A1 | 1/1998 |
| EP | 0 822 185 A1 | 2/1998 |
| EP | 0 955 299 A1 | 11/1999 |
| EP | 1 092 716 | 4/2001 |
| EP | 1 156 045 A1 | 11/2001 |
| FR | 2 244 499 A1 | 4/1975 |
| FR | 2 777 886 A1 | 10/1999 |
| FR | 2 799 756 A1 | 4/2001 |
| GB | 1 321 433 | 6/1973 |
| WO | 94/13637 A1 | 6/1994 |
| WO | 94/14434 A1 | 7/1994 |
| WO | 94/26738 A1 | 11/1994 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | 96/32379 A1 | 10/1996 |
| WO | 97/09308 A1 | 3/1997 |
| WO | 97/43260 A1 | 11/1997 |
| WO | 97/48697 A1 | 12/1997 |
| WO | 98/08818 A1 | 3/1998 |
| WO | 99/28297 A1 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58519 A1 | 11/1999 |
| WO | 99/61435 A1 | 12/1999 |
| WO | 00/32180 A2 | 6/2000 |
| WO | 00/35919 A1 | 6/2000 |
| WO | 00/46195 A1 | 8/2000 |
| WO | 00/46197 A1 | 8/2000 |
| WO | 00/64876 A1 | 11/2000 |
| WO | 00/64888 A1 | 11/2000 |
| WO | 01/12187 A2 | 2/2001 |
| WO | 02/30895 A1 | 4/2002 |
| WO | 02/072549 A1 | 9/2002 |
| WO | 03/000253 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online], [retrieved on Jul. 6, 2007]. Retrieved from the Internet, URL; http://en.wikipedia.org/wiki/Cancer>.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/condtions/09/24/alzheimers.drug.ap/indexhtml>.*
U.S. Appl. No. 10/947,711, filed Sep. 23, 2004, Gopalsamy et al.

Aggarwal et al., "A catalytic antibody programmed for torsional activation of amide bond hydrolysis," *Chem. Eur. J.*, Jan. 25, 2003, 9(13), 3132-3142.
Aznar, J. et al., "Role of Plasminogen Activator Inhibitor Type 1 in the Pathogenesis of Coronary Artery Diseases," *Haemostasis*, 1994, 24, 243-251.
Ballantine, J. A., "The Chemistry of Bacteria," *Journal of the Chemical Society Abstracts*, 1957, 2222-2227.
Bell M. R. (1970): STN International CAPLUS database, Columbus (Ohio), Accession No. 1970:66807.
Biemond, B. J. et al., "Thrombolysis and Reocclusion in Experimental Jugular Vein and Coronary Artery Thrombosis," *Circulation*, 1995, 91, 1175-1181.
Carmeliet, P. et al., "Plasminogen Activator Inhibitor-1 Gene-deficient Mice," *Journal of Clinical Investigation*, Dec. 1993, 92, 2756-2760.
Charlton, Peter, "The status of plasminogen activator inhibitor-1 as a therapeutic target," Expert *Opinion On Investigational Drugs*, May 1997, 6(5), 539-554.
Crandall, D. L. et al., "Characterization and comparative evaluation of a structurally unique PAI-1 inhibitor exhibiting oral in-vivo efficacy," *Journal of Thrombosis and Haemostasis*, Mar. 17, 2004, 2, 1-7.
Da Settimo, A. "Reaction of indole with bromine," *J. Org. Chem.*, 1970, 35(8), 2546-2551.
Daci, E. et al., "Mice Lacking the Plasminogen Activator Inhibitor 1 are Protected from Trabecular Bone Loss Induced by Estrogen Deficiency," *Journal of Bone and Mineral Research*, Nov. 8, 2000, 15(8), 1510-1516.
Delgado et al., Journal of Organic Chemistry (1993), 58(10), pp. 2862-2866.
Dillard R. D. et al., "Indole Inhibitors of Human Nonpancreatic Secretory Phospholipase $A_2$ 1. Indole-3-Acetamides", *Journal of Medicinal Chemistry*, American Chemical Society, 39(26), 5119-5136.
Guzzo, P.R. et al., "Synthesis of a conformationally constrained threonine-valine dipeptide mimetic: design of a potential inhibitor of plasminogen activator inhibitor-1," *Tetrahedron Letters*, 2002, 43(1), 41-43.
Hercelin et al. (1984): STN International CAPLUS database, Columbus (Ohio), Accession No. 1984-73988.
Hipskind, P. A. et al., "Potent and selective 1,2,3-trisubstituted indole NPY Y-1 antagonists," *J. Med. Chem.*, 1997, 40(23), 3712-3714.
Julia et al., CA 57:49169, 1962.
Krishnamurti, C. et al., "Plasminogen Activator Inhibitor: A Regulator of Ancrod-Induced Fibrin Desposition in Rabbits," *Blood*, Mar. 1987, 69(3), 798-803.
Levi, M. et al., "Inhibition of Plasminogen Activator Inhibitor-1 Activity Results in Promotion of Endogenous Thrombolysis and Inhibition of Thrombus Experimental Thrombosis," *Circulation*, 1992, 85, 305-312.
Malamas, M. S. et al., "Antihyperglycemic activity of new 1,2,4-oxadiazolidine-3,5-diones," *Eur. J. Med. Chem.*, 2001, 36, 31-42.
Malamas, Michael S. et al, "Novel Benzofuran and Benzothiophene Biphenyls as Inhibitors of Protein Tyrosine Phosphatase 1B with Antihyperglycemic Properties" *Journal Of Medicinal Chemistry*, 2000, 43(7), 1293-1310, XP002216395.
Moody et al., CA 120:298300, 1994.
Nordt, T. K. et al., "Differential Regulation by Troglitazone of Plasminogen Activator Inhibitor Type 1 in Human Hepatic and Vascular Cells," *Journal of Clinical Endocrinology and Metabolism*, 2000, 85(4), 1563-1568.
Reilly, C. et al., "Both Circulating and Clot-Bound Plasminogen Activator-1 Inhibit Endogenous Fibrinolysis in the Rat," *Arteriosclerosis and Thrombosis*, Sep./Oct. 1991, 11(5), 1276-1286.
Rocha, E. et al., "The Relationship Between Impaired Fibrinolysis and Coronary Heart Disease," *Fibrinolysis*, 1994, 8, 294-303.
Shengeliya, M. S. et al., "N-Glycosides of 5-amino-2-(ethoxycarbonyl)indole," *Zhurnal Organicheskoi Khimii*, 1986, 22(9), 1868-1873.
Krishnamurti et al., "Plasminogen activator inhibitor: a regulators of ancrod-induced fibrin deposition in rabbits", Blood, 1987, 69: 798-803.

Reilly et al., "Both ciruclating and clot-bound plasminogen activator inhibitor-1 inhibit endogenous fibrinolysis in the rat". Arterioscler. Thromb. Vasc. Biol., 1991, 11:1276-1286.

Carmeliet et al., "Plasminogen activator inhibitor-1 gene-deficient mice. II. Effects on hemostasis, thrombosis, and thrombolysis", Journal of Clinical Investigation, 1993, 92: 2756-2760.

Rocha et al., "The relationship between impaired fibrinolysis and coronary heart disease: a role for PAI-1", Fibrinolysis, 1994, 8:294-303.

Aznar et al., "Role of plasminogen activator inhibitor type 1 in the pathogenesis of coronary artery diseases", Haemostasis, 1994, 24(4):243-51.

Biemond et al., "Thrombolysis and Reocclusion in Experimental Jugular Vein and Coronary Artery Thrombosis : Effects of a Plasminogen Activator Inhibitor Type 1—Neutralizing Monoclonal Antibody", Circulation, 1995, 91: 1175-1181.

Levi et al., "Inhibition of plasminogen activator inhibitor-1 activity results in promotion of endogenous thrombolysis and inhibition of thrombus extension in models of experimental thrombosis", Circulation, 1992, 85:305-312.

Takazoe et al., "Increased plasminogen activator inhibitor activity and diabetes predict subsequent coronary events in patients with angina pectoris", Ann. Med., 2001, 33(3):206-12.

Wind et al., "Epitope mapping for four monoclonal antibodies against human plasminogen activator inhibitor type-1: implications for antibody-mediated PAI-1-neutralization and vitronectin-binding", Eur. J. Biochem., 2001, 268:1095-1106.

Thogersen et al., "High plasminogen activator inhibitor and tissue plasminogen activator levels in plasma precede a first acute myocardial infarction in both men and women: evidence for the fibrinolytic system as an independent primary risk factor", Circulation, 1998, 98:2241-2247.

Schneiderman et al., "Increased type 1 plasminogen activator inhibitor gene expression in atherosclerotic human arteries", Proc. Natl. Acad. Sci., 1992, 89: 6998-7002.

Sobel, "The potential influence of insulin and plasminogen activator inhibitor type 1 on the formation of vulnerable atherosclerotic plaques associated with type 2 diabetes",Proc. Assoc. Am. Physicians, 1999, 111(4):313-8.

Roldan et al., "Hypofibrinolysis in atrial fibrillation", American Heart Journal, 1998, 136(6): 956-960.

Albers, "Advances in intravenous thrombolytic therapy for treatment of acute stroke", Neurology, 2001, 57(suppl 2):S77-S81.

Juhan-Vague et al., "Deficient t-PA release and elevated PA inhibitor levels in patients with spontaneous or recurrent deep venous thrombosis", Thromb. Haemost., 1987, 57: 67-72.

Berry et al., "Antithrombotic activity of a monoclonal antibody inducing the substrate form of plasminogen activator inhibitor type 1 in rat models of venous and arterial thrombosis",British Journal of Pharmacology, 1998, 125: 29-34.

Juhan-Vague et al., "PAI-1 obesity, insulin resistance and risk of cardiovascular events", Thromb. Haemost., 1997, 78(1):656-60.

Malamas et al., "New azolidinediones as inhibitors of protein tyrosine phosphatase 1B with antihyperglycemic properties", J. Med. Chem., 2000, 43:995-1010.

Malamas et al., "Antihyperglycemic activity of new 1,2,4-oxadiazolidine-3,5-diones", Eur. J. Med. Chem. 2001, 36:31-42.

Takanashi and Inukai, "Insulin resistance and changes in the blood coagulation-fibrinolysis system after a glucose clamp technique in patients with type 2 diabetes mellitus", Journal of Medicine, 2000, 3:45-62.

Hamano et al., "Expression of glomerular plasminogen activator inhibitor type 1 in glomerulonephritis", American Journal of Kidney Diseases, 2002, 39(4): 695-705.

Lahlou et al., "Chronic graft dysfunction in renal transplant patients: potential role of plasminogen activator inhibitor type 1", Transplantation, 2002, 73: 1290-1295.

Ashitani et al., "Elevated plasma procoagulant and fibrinolytic markers in patients with chronic obstructive pulmonary disease", Internal Medicine, 2002,41(3): 181-185.

Hamsten et al., "Plasminogen activator inhibitor in plasma: risk factor for recurrent myocardial infarction", Lancet, 1987, 2:3-9.

Siemens et. al., "Course of molecular hemostatic markers during and after different surgical procedures", J. Clin. Anesthesia, 1999, 11: 622-629.

Koh et al., "Effects of hormone-replacement therapy on fibrinolysis in postmenopausal women", New Engl. J. Med., 1997, 336: 683-690.

Atiomo et al., "Immunohistochemical detection of plasminogen activator inhibitor-1 in polycystic ovaries", Gynecol. Endocrinol., 2000, 14:162-168.

Glueck et al., "Continuing metformin throughout pregnancy in women with polycystic ovary syndrome appears to safely reduce first-trimester spontaneous abortion: a pilot study", Fertility and Sterility, 2001, 75(1): 46-52.

Nordt, "Differential regulation by troglitazone of plasminogen activator inhibitor type 1 in human hepatic and vascular cells", Journal of clinical Endocrinology and Metabolism, 2000, 85(4): 1563-1568.

Daci, "Mice lacking the plasminogen activator inhibitor 1 are protected from trabecular bone loss induced by estrogen deficiency", Journal of Bone and Mineral Research, 2000, 15(8): 1510-1516.

Periz and Fortini, "Proteolysis in Alzheimer's disease. Can plasmin tip the balance?", EMBO Reports, 2000, 1:477-478.

Tucker et al., "The plasmin system is induced by and degrades amyloid-beta aggregates", J. Neurosci., 2000, 20:3937-3946.

Kingston et al., "In vitro stimulation of tissue-type plasminogen activator by Alzheimer amyloid beta-peptide analogues", Nat. Med. 1995, 1:138-142.

Wnendt et al., "Amyloid beta peptides stimulate tissue-type plasminogen activator but not recombinant prourokinase", Thrombosis Res., 1997, 8:217-224.

Van Nostrand and Porter, "Plasmin cleavage of the amyloid beta-protein: alteration of secondary structure and stimulation of tissue plasminogen activator activity", Biochemistry, 1999, 38:11570-11576.

Exley and Korchazhkina, "Plasmin cleaves Abeta42 in vitro and prevents its aggregation into beta-pleated sheet structures", Neuroreport, 2001, 12:2967-2970.

Tucker et al., "Tissue plasminogen activator requires plasminogen to modulate amyloid-beta neurotoxicity and deposition", J. Neurochem., 2000, 75:2172-2177.

Tsirka et al., "An extracellular proteolytic cascade promotes neuronal degeneration in the mouse hippocampus", J. Neurosci.,1997, 17:543-552.

Seeds et al., "Neuronal migration is retarded in mice lacking the tissue plasminogen activator gene", Proc. Natl. Acad. Sci., 1999, 96:14118-14123.

McGeer and McGeer, "the inflammatory response system of brain: implications for therapy of Alzheimer and other neurodegenerative diseases", Brain Res. Rev., 1995, 21:195-218.

Ledesma et al., "Brain plasmin enhances APP alpha-cleavage and Abeta degradation and is reduced in Alzheimer's disease brains", EMBO Reports, 2000, 1:530-535.

Simons et al., "Cholesterol depletion inhibits the generation of beta-amyloid in hippocampal neurons", Proc. Natl. Acad. Sci., 1998, 95:6460-6464.

Melchor et al., "The tissue plasminogen activator-plasminogen proteolytic cascade accelerates amyloid-beta (Abeta) degradation and inhibits Abeta-induced neurodegeneration",J. Neurosci., 2003, 23: 8867-8871.

Tucker et al., "Urokinase-type plasminogen activator inhibits amyloid-beta neurotoxicity and fibrillogenesis via plasminogen", J. Neurosci. Res., 2002, 70:249-255.

Kim et al., "Nonproteolytic neuroprotection by human recombinant tissue plasminogen activator", Science, 1999, 284:647-650.

Fay et al., "Human plasminogen activator inhibitor-1 (PAI-1) deficiency: characterization of a large kindred with a null mutation in the PAI-1 gene", Blood, 1997, 90:204-208.

Carmeliet et al., "Biological effects of disruption of the tissue-type plasminogen activator, urokinase-type plasminogen activator, and plasminogen activator inhibitor-1 genes in mice", Ann. NY Acad Sci, 1995, 748:367-381.

Frandsen et al., "Plasminogen activator inhibitor type 1 (PAI-1) in cancer: a potential new target for antiinvasive and antimetastatic therapy", Drugs of the Future, 1998, 23(8): 873-883.

Isogai, et al., "Plasminogen activator inhibitor-1 promotes angiogenesis by stimulating endothelial cell migration toward fibronectin", Cancer Research, 2001, 61(14): 5587-5594.

Qu et al., "Clinical significance of the expression of urokinase type plasminogen activator and plasminogen activator inhibitor in cervical carcinomas", China J. Cancer Prev. Treat., 2003, 10(8): 821-824.

Lool et al., "Pooled analysis of prognostic impact of urokinase-type plasminogen activator and its inhibitor PAI-1 in 8377 breast cancer patients", Journal of the National Cancer Institute, 2002, 94(2): 116-128.

Chazaud et al., "Promigratory effect of plasminogen activator inhibitor-1 on invasive breast cancer cell populations", American Journal of Pathology, 2002, 160(1): 237-246.

Egelund et al., "A regulatory hydrophobic area in the flexible joint region of plasminogen activator inhibitor-1, defined with fluorescent activity-neutralizing ligands. Ligand-induced serpin polymerization", Journal of Biological Chemistry, 2001, 276(16): 13077-13086.

Bianchi et al., "Immunohistochemical localization of the plasminogen activator inhibitor-1 in breast cancer", International Journal of Cancer, 1995, 60(5): 597-603.

Zhao et al., "Immunohistochemical expression of uPA, PAI-1, cathepsin D and apoptotic cells in ductal carcinoma in situ of the breast", Breast cancer, (Tokyo, Japan), 2002, 9(2): 118-26.

* cited by examiner

SUBSTITUTED 3-CARBONYL-1H-INDOL-1YL ACETIC ACID DERIVATIVES AS INHIBITORS OF PLASMINOGEN ACTIVATOR INHIBITOR-1 (PAI-1)

This application is a divisional of application Ser. No. 10/731,723 filed on Dec. 9, 2003 which claims priority from co-pending provisional application Ser. No. 60/432,107 filed on Dec. 10, 2002. The entire disclosures of each application are hereby incorporated by reference.

This invention relates to substituted 3-carbonyl-1H-indol-1-yl acetic acid derivatives as inhibitors of plasminogen activator inhibitor-1 (PAI-1) and as therapeutic compositions for treating conditions resulting from fibrinolytic disorders such as deep vein thrombosis and coronary heart disease, and pulmonary fibrosis.

BACKGROUND OF INVENTION

Plasminogen activator inhibitor-1 (PAI-1) is a major regulatory component of the plasminogen-plasmin system. PAI-1 is the principal physiologic inhibitor of both tissue type plasminogen activator (tPA) and urokinase type plasminogen activator (uPA). Elevated plasma levels of PAI-1 have been associated with thrombotic events as indicated by animal experiments (Krishnamurti, *Blood*, 69, 798 (1987); Reilly, *Arteriosclerosis and Thrombosis*, 11, 1276 (1991); Carmeliet, *Journal of Clinical Investigations*, 92, 2756 (1993)) and clinical studies (Rocha, *Fibrinolysis*, 8, 294, 1994; Aznar, *Haemostasis* 24, 243 (1994)). Antibody neutralization of PAI-1 activity resulted in promotion of endogenous thrombolysis and reperfusion (Biemond, *Circulation*, 91, 1175 (1995); Levi, *Circulation* 85, 305, (1992)). Elevated levels of PAI-1 have also been implicated in diseases of women such as polycystic ovary syndrome (Nordt, *Journal of Clinical Endocrinology and Metabolism*, 85, 4, 1563 (2000)) and bone loss induced by estrogen deficiency (Daci, *Journal of Bone and Mineral Research*, 15, 8, 1510 (2000)). Accordingly, agents that inhibit PAI-1 would be of utility in treating conditions originating from fibrinolytic disorder such as deep vein thrombosis, coronary heart disease, pulmonary fibrosis, polycystic ovary syndrome, etc.

WO 99/43654 and WO 99/43651 describe indole derivatives of formula I as inhibitors of phospholipase enzymes useful in preventing inflammatory conditions:

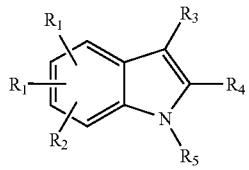

(I)

WO 2000/44743 discloses TGF-β production inhibitors of formula I:

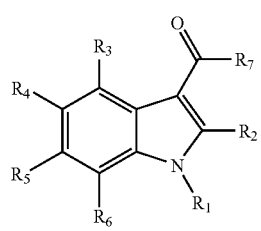

(I)

where $R_1$ and $R_2$ are each independently hydrogen, optionally substituted alkyl, acyl, optionally substituted aryl or aromatic heterocyclic group and $R_7$ is an optionally substituted cyclic amino or azabicycloalkylamino.

WO 97/48697 describes substituted azabicyclic compounds inclusive of indoles, 2,3-dihydro-1H-indoles, and benzimidazoles of formula (I) for the treatment of conditions ameliorated by the administration of an inhibitor of tumor necrosis factor:

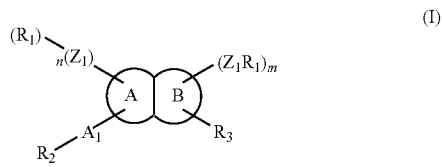

(I)

where A is a five-membered aza heterocycle;

B is a six membered aza heterocycle or an optionally substituted benzene ring;

$Z_1$ is a chemical bond, O, S, or NH;

$A_1$ is a chemical bond, alkyl of 1-6 carbons, alkenylene of 2-6 carbons, or alkynylene of 2-6 carbons;

$R_1$ is hydrogen or optionally substituted alkyl of 2-6 carbons, lower alkenyl or lower alkynyl;

$R_2$ is hydrogen, alkenyl, alkyl, alkylsulfinyl, alkylsulphonyl, alkylthio, aryl, arylalkoxy, arylalkylsulphinyl, arylalkylsulphonyl, arylalkylthio, aryloxy, arylsulphinyl, arylsulphonyl, arylthio, —CN, cycloalkenyl, cycloalkenoxy, cycloalkyl, cycloalkyloxy, heteroaryl, heteroarylalkyloxy, heteroaryloxy, —OH, —SO$_2$NR$_4$R$_5$, —NR$_4$SO$_2$R$_5$, —NR$_4$R$_5$, —C(O)R$_5$, —C(O)C(O)R$_5$, —O(C=O) NR$_4$R$_5$, —C(O)OR$_5$, or —O(C=O)NR$_4$R$_5$, and $R_3$ is carboxamide, acyl, substituted alkenyl, substituted alkyl, acylamino, oximino, alkynyl, ketomethyl, aminoalkyl, sulfonylmethyl, sulfinylmethyl, CF$_2$OR, alkylamino, alkoxy, alkylsulfanyl, sulfinyl, acyloxy, sulfonyl, OCF$_2$R, azo, aminosulfonyl, sulfonylamino, or aminooxalyl.

U.S. Pat. No. 5,612,360 describes tetrazolylphenyl-substituted heterocycles of formula (I) as angiotensin II inhibitors.

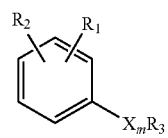

(I)

where: $R_1$ is —COOH, —S(O)$_3$H, —PO$_3$H$_2$, —C(O)NHSO$_2$R$_8$, or 5-tetrazolyl;

$R_2$ is hydrogen, —OH, —OAc, halogen, alkyl of 1-4 carbons, or alkoxy of 1-4 carbons;

$R_3$ is substituted benzimidazole, indazole, or

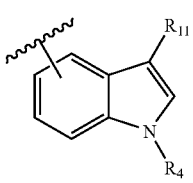

$R_4$ is:

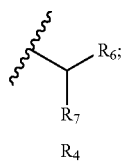

$R_6$ may be $(CH_2)_pR_1$, $CONH(C_1$ to $C_4$ alkyl), or $CONH(C_1$ to $C_4$ trifluoroalkyl) where p is 0, 1, 2, 3 or 4.

$R_7$ is alkyl, trifluoroalkyl, alkenyl, or trifluoroalkenyl all of 4-9 carbons;

$R_{11}$ is hydrogen, alkyl of 1-4 carbons, halogen, or $(CH_2)_n$ phenyl; X is $-(CH_2)_mCONH-$, $-(CH_2)_mNHCO-$, $-CH_2-$, $-O-$, $-NH-$, or $-(CH_2)_mCO-$; and m is 0 or 1, where m is 0 or 1 and n is 1, 2 or 3.

FR 2,054,450 describes carboxymethyl indoles of formula (I) as anti-inflammatory agents:

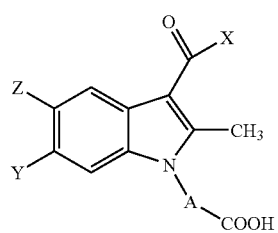

where: A is linear alkyl;
X is phenyl, optionally substituted with chlorine, alkyloxy, alkylthio, or alkylsulfonyl;
Y is alkyl; and
Z is hydrogen or alkyloxy.

SUMMARY OF THE INVENTION

This invention relates to compounds of formula (I):

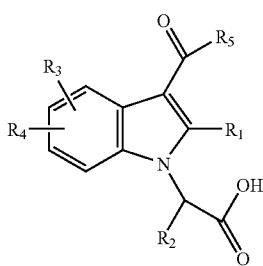

wherein:
$R_1$ is hydrogen, $C_2-C_6$ alkyl, $C_3-C_6$ cycloalkyl, $-CH_2-C_3-C_6$ cycloalkyl, or $C_1-C_3$ perfluoroalkyl, wherein the alkyl and cycloalkyl groups may be optionally substituted with halogen, $-CN$, $C_1-C_6$ alkoxy, $-OH$, $-NH_2$, or $-NO_2$;

$R_2$ is hydrogen, $C_1-C_8$ alkyl, $C_3-C_6$ cycloalkyl, $-CH_2-C_3-C_6$ cycloalkyl, thienyl, $CH_2$-thienyl, furanyl, $CH_2$-furanyl, oxazoyl, $CH_2$-oxazoyl, phenyl, benzyl, $CH_2$-naphthyl, wherein the alkyl group and rings of the cycloalkyl, thienyl, furanyl, oxazoyl, phenyl, benzyl, and napthyl groups may be optionally substituted with from 1 to 3 groups selected from halogen, $C_1-C_3$ alkyl, $C_1-C_3$ perfluoroalkyl, $O-C_1-C_3$ perfluoroalkyl, $S-C_1-C_3$ perfluoroalkyl, $C_1-C_3$ alkoxy, $-OCHF_2$, $-CN$, $-COOH$, $-CH_2CO_2H$, $-C(O)CH_3$, $-CO_2R_6$, $-C(O)NH_2$, $-S(O)_2CH_3$, $-OH$, $-NH_2$, or $-NO_2$;

$R_3$ is hydrogen, halogen, $C_1-C_6$ alkyl, $C_1-C_3$ perfluoroalkyl, preferably $-CF_3$, $C_1-C_6$ alkoxy, $C_3-C_6$ cycloalkyl, $-CH_2-C_3-C_6$ cycloalkyl, $-NH_2$, or $-NO_2$;

$R_4$ is $C_3-C_8$ alkyl, $C_3-C_6$ alkenyl, $C_3-C_6$ alkynyl, $C_3-C_6$ cycloalkyl, $-CH_2-C_3-C_6$cycloalkyl, thienyl, furanyl, oxazoyl, phenyl, benzo[b]furan-2-yl, benzo[b]thien-2-yl, benzo[1,3]dioxol-5-yl, naphthyl, wherein the alkyl group and the rings of the cycloalkyl, thienyl, furanyl, oxazoyl, phenyl, benzofuranyl, benzothienyl, and naphthyl groups may be optionally substituted by from 1 to 3 groups selected from halogen, $C_1-C_3$ alkyl, $C_1-C_3$ perfluoroalkyl, $O-C_1-C_3$ perfluoroalkyl, $S-C_1C_3$ perfluoroalkyl, $C_1-C_3$ alkoxy, $-OCHF_2$, $-CN$, $-COOH$, $CH_2CO_2H$, $-C(O)CH_3$, $-C(O)OR_6$, $-C(O)NH_2$, $-S(O)-_2CH_3$, $-OH$, $-NH_2$, or $-NO_2$;

$R_5$ is $C_1-C_8$ alkyl, $C_3-C_6$ cycloalkyl, $-CH_2-C_3-C_6$ cycloalkyl, pyridinyl, $-CH_2$-pyridinyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, naphthyl, $CH_2$-naphyl, 9H-fluoren-1-yl, 9H-fluoren-4-yl, 9H-fluoren-9-yl, 9-fluorenone-1-yl, 9-fluorenone-2-yl, 9-fluorenone-4-yl, $CH_2$-9H-fluoren-9-yl, wherein the alkyl group and the rings of the cycloalkyl, pyridinyl, thienyl, furanyl, oxazoyl, phenyl, benzyl, benzofuranyl, benzothienyl, napthyl, fluorenyl, and fluorenone groups may be optionally substituted by from 1 to 3 groups selected from halogen, $C_1-C_3$ alkyl, $C_3-C_6$ cycloalkyl, $C_1-C_3$ perfluoroalkyl, $-O-C_1-C_3$ perfluoroalkyl, $-S-C_1-C_3$ perfluoroalkyl, $C_1-C_3$ alkoxy, phenoxy, $-OCHF_2$, $-CN$, $-COOH$, $-CH_2CO_2H$, $-C(O)CH_3$, $-CO_2R_6$, $-C(O)NH_2$, $-S(O)_2CH_3$, $-OH$, $-NH_2$, or $-NO_2$, wherein the phenoxy group may be optionally substituted by from 1 to 3 groups selected from halogen, $C_1-C_3$ alkyl, or $C_1-C_3$ perfluoroalkyl; and $R_6$ is $C_1-C_6$ alkyl, $C_3-C_6$ cycloalkyl, $-CH_2-C_3-C_6$ cycloalkyl, or benzyl;

or a pharmaceutically acceptable salt or ester form thereof.

DETAILED DESCRIPTION OF THE INVENTION

Preferred compounds of the present invention are those of formula (I) wherein $R_1-R_3$ and $R_5-R_6$ are as defined above, and $R_4$ is thienyl, furanyl, oxazoyl, phenyl, benzo[b]furan-2-yl, benzo[b]thien-2-yl, benzo[1,3]dioxol-5-yl or naphthyl, wherein the rings of the thienyl, furanyl, oxazoyl, phenyl, benzofuranyl, benzothienyl, and napthyl groups may be optionally substituted by from 1 to 3 groups selected from halogen, $C_1-C_3$ alkyl, $C_1-C_3$ perfluoroalkyl, $-O-C_1-C_3$ perfluoroalkyl, $-S-C_1-C_3$ perfluoroalkyl, $C_1-C_3$ alkoxy, $-OCHF_2$, $-CN$, $-COOH$, $-CH_2CO_2H$, $-C(O)CH_3$, $-CO_2R_6$, $-C(O)NH_2$, $-S(O)_2CH_3$, $-OH$, $-NH_2$, or $-NO_2$;

or a pharmaceutically acceptable salt or ester form thereof.

Specific compounds according to this invention include:
[3-(4-chlorobenzoyl)-5-(4-chlorophenyl)-1H-indol-1yl] acetic acid;
[3-(benzo[b]thiophene-2-carbonyl)-5-(4-methylphenyl)-1H-indol-1-yl]acetic acid; and
[3-(4-chlorobenzoyl)-5-(4-methylphenyl)-1 H-indol-1yl] acetic acid, or a pharmaceutically acceptable salt or ester form thereof.

The preferred salt forms of the compounds herein include but are not limited to sodium salts, and potassium salts. Other useful salt forms of these compounds include those formed with pharmaceutically acceptable inorganic and organic bases known in the art. Salt forms prepared using inorganic bases include hydroxides, carbonates or bicarbonates of the therapeutically acceptable alkali metals or alkaline earth methals, such as sodium potassium, magnesium, calcium and the like. Acceptable organic bases include amines, such as benzylzmine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Also useful are alkylene diamines containing up to 6 carbon atoms, such as hexamethylenediamine; cyclic saturated or unsaturated bases containing up to 6 carbon atoms, including pyrrolidine, peperidine, morpholine, piperazine and their N-alkyl and N-hydroxyalkyl derivatives, such as N-methyl-morpholine and N-(2-hyroxyethyl)-piperidine, or pyridine. Quaternary salts may also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-dimethylmorpholinium, N-mehtyl-N-(2-hydroxyethyl)-morpholinium, or N,N-dimethylpiperidinium salt forms. These salt forms may be prepared using the acidic compound(s) of Formula I and procedures known in the art.

Ester forms of the compounds of this invention include straight chain alkyl esters having from 1 to 6 carbon atoms or branched chain alkyl groups containing 3 or 6 carbon atoms, including methyl, ethyl, propyl, butyl, 2-methylpropyl and 1,1-dimethylethyl esters. Other esters useful with this invention include those of the formula —COOR$_7$ wherein R$_7$ is selected from the formulae:

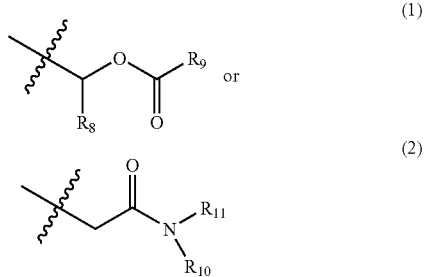

wherein R$_8$, R$_9$, R$_{10}$, R$_{11}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Among the preferred ester forms of the compounds herein include but not limited to $C_1$-$C_6$ alkyl esters, $C_3$-$C_6$ branched alkyl esters, benzyl esters, etc.

As used herein, the terms alkyl, alkenyl and alkynyl include both straight chain as well as branched claim chains. Preferably, the $C_1$-$C_3$ perfluoroalkyl substituent is —$CF_3$; the —O—$C_1$-$C_3$ perfluoroalkyl substituent is $OCF_3$; and the —S—C—$C_3$ perfluoroalkyl substituent is —$SCF_3$.

As used herein, "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryl groups include phenyl, naphthyl and the like. As used herein, "heteroaryl" refers to a monocyclic or bicyclic aromatic group of from 1 to carbon atoms and 1 to 4 heteroatoms selected from oxygen, nitrogen and sulfur within at least one ring (if there is more than one ring). Such heteroaryl groups can have a single ring, such as pyridyl, pyrrolyl or furyl groups, or multiple condensed rings, such as indolyl, indolizinyl, benzofuranyl or benzothienyl groups. Preferred heteroaryls include pyridyl, pyrrolyl and furyl.

Unless otherwise limited by the definition for the aryl or heteroaryl groups herein, such groups can optionally be substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. Substituents on the alkyl, alkenyl, alkynyl, thioalkoxy and alkoxy groups mentioned above include halogens, CN, OH, and amino groups. Preferred substituents on the aryl groups herein include alkyl, alkoxy, halo, cyano, nitro, trihalomethyl, and thioalkoxy.

The compounds of the present invention are inhibitors of the serine protease inhibitor PAI-1, and are therefore useful in the treatment, inhibition, prevention or prophylaxis in a mammal, preferably in a human, of those processes which involve the production and/or action of PAI-1. Thus, the compounds of the invention are useful in the treatment or prevention of noninsulin dependent diabetes mellitus and cardiovascular disease caused by such condition, and prevention of thrombotic events associated with coronary artery and cerebrovascular disease. These compounds are also useful for inhibiting the disease process involving the thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery (such as joint replacement), and peripheral arterial occlusion. These compounds are also useful in treating stroke associated with or resulting from atrial fibrillation.

The compounds of the invention may also be used in the treatment of diseases associated with extracellular matrix accumulation, including, but not limited to, renal fibrosis, chronic obstructive pulmonary disease, polycystic ovary syndrome, restenosis, renovascular disease and organ transplant rejection.

The compounds of the invention may also be used in the treatment of malignancies, and diseases associated with neoangiogenesis (such as diabetic retinopathy).

The compounds in the invention may also be used in conjunction with and following processes or procedures involving maintaining blood vessel patency, including vascular surgery, vascular graft and stent patency, organ, tissue and cell implantation and transplantation.

The compounds in the invention may also be useful in the treatment of inflammatory diseases, septic shock and the vascular damage associated with infections.

The compounds of the invention are useful for the treatment of blood and blood products used in dialysis, blood storage in the fluid phase, especially ex vivo platelet aggregation. The present compounds may also be added to human plasma during the analysis of blood chemistry in hospital settings to determine the fibrinolytic capacity thereof.

The compounds in the present invention may also be used in combination with prothrombolytic, fibrinolytic and anticoagulant agents.

The compounds of the present invention may also be used to treat cancer including, but not limited to, breast and ovarian cancer, and as imaging agents for the identification of metastatic cancers.

The compounds of the invention may also be used in the treatment of Alzheimer's disease. This method may also be characterized as the inhibition of plasminogen activator by PAI-1 in a mammal, particularly a human, experiencing or subject to Alzheimer's disease. This method may also be characterized as a method of increasing or normalizing levels of plasmin concentration in a mammal, particularly those experiencing or subject to Alzheimer's disease.

The compounds of the invention may be used for the treatment of myelofibrosis with myeloid metaplasia by regulating stromal cell hyperplasia and increases in extracellular matrix proteins.

The compounds of the invention may also be used in conjunction with protease inhibitor—containing highly active antiretroviral therapy (HAART) for the treatment of diseases which originate from fibrinolytic impairment and hyper-coagulability of HIV-1 infected patients receiving such therapy.

The compounds of the invention may be used for the treatment of diabetic nephropathy and renal dialysis associated with nephropathy.

The compounds of the invention may be used to treat cancer, septicemia, obesity, insulin resistance, proliferative diseases such as psoriasis, improving coagulation homeostasis, cerebrovascular diseases, microvascular disease, hypertension, dementia, osteoporosis, arthritis, asthma, heart failure, arrhythmia, angina, and as a hormone replacement agent, treating, preventing or reversing progression of atherosclerosis, Alzheimer's disease, osteoporosis, osteopenia; reducing inflammatory markers, reducing C-reactive protein, or preventing or treating low grade vascular inflammation, stroke, dementia, coronary heart disease, primary and secondary prevention of myocardial infarction, stable and unstable angina, primary prevention of coronary events, secondary prevention of cardiovascular events, peripheral vascular disease, peripheral arterial disease, acute vascular syndromes, reducing the risk of undergoing a myocardial revascularization procedure, microvascular diseases such as nephropathy, neuropathy, retinopathy and nephrotic syndrome, hypertension, Type 1 and 2 diabetes and related diseases, hyperglycemia, hyperinsulinemia, malignant lesions, premalignant lesions, gastrointestinal malignancies, liposarcomas and epithelial tumors, proliferative diseases such as psoriasis, improving coagulation homeostasis, and/or improving endothelial function, and all forms of cerebrovascular diseases.

The compounds of the invention may be used for the topical applications in wound healing for prevention of scarring.

Methods for the treatment, inhibition, prevention or prophylaxis in a mammal of each of the conditions or maladies listed herein are part of the present invention. Each method comprises administering to a mammal in need thereof a pharmaceutically or therapeutically effective amount of a compound of this invention, or a pharmaceutically acceptable salt or ester form thereof.

Each of the methods described herein comprise administering to a mammal in need of such treatment a pharmaceutically effective amount of a compound of this invention, or a pharmaceutically acceptable salt or ester form thereof. It will be understood that a pharmaceutically effective amount of the compound will be at least the minimum amount necessary to provide an improvement in the symptoms or underlying causation of the malady in question or to inhibit or lessen the onset of symptoms of the malady.

Accordingly the present invention further comprises a method of inhibiting in a mammal plasminogen activator inhibitor type 1 (PAI-1) which comprises administering to a mammal in need thereof a pharmaceutically effective amount of a compound of Formula (I):

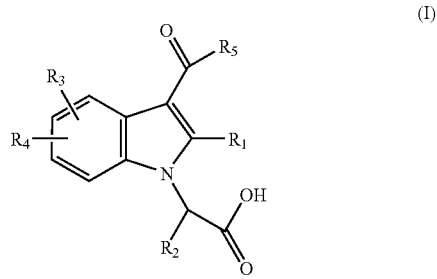

(I)

wherein, $R_1$ is hydrogen, $C_2$-$C_6$ alkyl, $C_3$-$C_6$ cycloalkyl, —$CH_2$—$C_3$-$C_6$ cycloalkyl, or $C_1$-$C_3$ perfluoroalkyl, wherein the alkyl and cycloalkyl groups may be optionally substituted with halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, —$CH_2$—$C_3$-$C_6$ cycloalkyl, thienyl, $CH_2$-thienyl, furanyl, $CH_2$-furanyl, oxazoyl, $CH_2$-oxazoyl, phenyl, benzyl, $CH_2$-naphthyl, wherein the alkyl group and rings of the cycloalkyl, thienyl, furanyl, oxazoyl, phenyl, benzyl, and napthyl groups may be optionally substituted with from 1 to 3 groups selected from halogen, $C_1$-$C_3$ alkyl, $C_1$-$C_3$ perfluoroalkyl, O—$C_1$-$C_3$ perfluoroalkyl, S—$C_1$-$C_3$ perfluoroalkyl, $C_1$-$C_3$ alkoxy, —$OCHF_2$, —CN, —COOH, —$CH_2CO_2H$, —$C(O)CH_3$, —$CO_2R_6$, —$C(O)NH_2$, —$S(O)_2CH_3$, —OH, —$NH_2$, or —$NO_2$;

$R_3$ is hydrogen, halogen, $C_1$-$C_6$ alkyl, $C_1$-$C_3$ perfluoroalkyl, preferably —$CF_3$, $C_1$-$C_6$ alkoxy, $C_3$-$C_6$ cycloalkyl, —$CH_2$—$C_3$-$C_6$ cycloalkyl, —$NH_2$, or —$NO_2$;

$R_4$ is $C_3$-$C_8$ alkyl, $C_3$-$C_6$ alkenyl, $C_3$-$C_6$ alkynyl, $C_3$-$C_6$ cycloalkyl, —$CH_2$—$C_3$-$C_6$ cycloalkyl, thienyl, furanyl, oxazoyl, phenyl, benzo[b]furan-2-yl, benzo[b]thien-2-yl, benzo[1,3]dioxol-5-yl, naphthyl, wherein the alkyl group and the rings of the cycloalkyl, thienyl, furanyl, oxazoyl, phenyl, benzofuranyl, benzothienyl, and napthyl groups may be optionally substituted by from 1 to 3 groups selected from halogen, $C_1$-$C_3$ alkyl, $C_1$-$C_3$ perfluoroalkyl, O—$C_1$-$C_3$ perfluoroalkyl, S—$C_1$-$C_3$ perfluoroalkyl, $C_1$-$C_3$ alkoxy, —$OCHF_2$, —CN, COOH, —$CH_2CO_2H$, —$C(O)CH_3$, —$C(O)OR_6$, —$C(O)NH_2$, —$S(O)$—$_2CH_3$, —OH, —$NH_2$, or —$NO_2$;

$R_5$ is $C_1$-$C_8$ alkyl, $C_3$-$C_6$ cycloalkyl, —$CH_2$—$C_3$-$C_6$ cycloalkyl, pyridinyl, —$CH_2$-pyridinyl, thienyl, $CH_2$-thienyl, furanyl, $CH_2$-furanyl, oxazoyl, $CH_2$-oxazoyl, phenyl, benzyl, benzo[b]furan-2-yl, benzo[b]thien-2-yl, benzo[1,3]dioxol-5-yl, naphthyl, $CH_2$-naphthyl, 9H-fluoren-1-yl, 9H-fluoren-4-yl, 9H-fluoren-9-yl, 9-fluorenone-1-yl, 9-fluorenone-2-yl, 9-fluorenone-4-yl, $CH_2$-9H-fluoren-9-yl, wherein the alkyl group and the rings of the cycloalkyl, pyridinyl, thienyl, furanyl, oxazoyl, phenyl, benzyl, benzofuranyl, benzothienyl, naphthyl, fluorenyl, and fluorenone groups may be optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, phenoxy, —OCHF$_2$, —CN, —COOH, —CH$_2$CO$_2$H, —C(O)CH$_3$, —CO$_2$R$_6$, —C(O)NH$_2$, —S(O)$_2$CH$_3$, —OH, —NH$_2$, or —NO$_2$, wherein the phenoxy group may be optionally substituted by from 1 to 3 groups selected from halogen, $C_1$-$C_3$ alkyl, or $C_1$-$C_3$ perfluoroalkyl; and $R_6$ is $C_1$-$C_6$ alkyl, $C_3$-$C_6$ cycloalkyl, —CH$_2$—$C_3$-$C_6$ cycloalkyl, or benzyl;

or a pharmaceutically acceptable salt or ester form thereof.

PROCESS OF THE INVENTION

The compounds of the present invention can be readily prepared according to the following reaction scheme or modification thereof as would be recognized by one skilled in the art using readily available starting materials, reagents and conventional synthetic procedures. It is also possible to make use of variants of these process steps, which in themselves are known to and well within the preparatory skill of the medicinal chemist. In the following reaction schemes, $R_1$-$R_6$ are selected from the groups defined above. $R_{12}$ and $R_{13}$ are each independently hydrogen, halogen, $C_1$-$C_3$ alkyl, $C_1$-$C_3$ perfluoroalkyl, preferably —CF$_3$, —O—$C_1$-$C_3$ perfluoroalkyl, preferably —OCF$_3$, —S—$C_1$-$C_3$ perfluoroalkyl, preferably —SCF$_3$, $C_1$-$C_3$ alkoxy, —OCHF$_2$, —C(O)CH$_3$, —C(O)NH$_2$, —S(O)$_2$CH$_3$, —OH, —NH$_2$, or —NO$_2$;

Method A

In Method A, indole, substituted on the benzene ring with bromide, iodine, or triflate, is cross-coupled with an aryl boronic acid in the presence of a palladium catalyst, such as Pd(PPh$_3$)$_4$, a base, such as Na$_2$CO$_3$ or NaHCO$_3$, in a solvent, such as water, dioxane, THF, toluene, methanol or ethanol, or in a mixed co-solvent system comprising two or more of the aforesaid solvents, at 50-110° C. Boronic acid derivatives of benzene, furan, thiophene, benz[b]thiophene and napthylene are described in the literature and many are presently commercially available. The resulting aryl substituted indole may be alkylated on nitrogen using methyl bromoacetate in the presence of a base, such as NaH or KOt-Bu, in an inert solvent, such as THF or DMF. The resulting aryl indo-1-yl acetic acid methyl ester is acylated at the C-3 position by an acid chloride in a solvent, such as dichloromethane (DCM) or dichloroethane (DCE), in the presence of a Lewis acid, such as SnCl$_4$ at –40 to +25° C. The methyl ester may be hydrolyzed with base and purified by chromatography or by HPLC to afford the 1H-indol-1-yl acetic acid compounds.

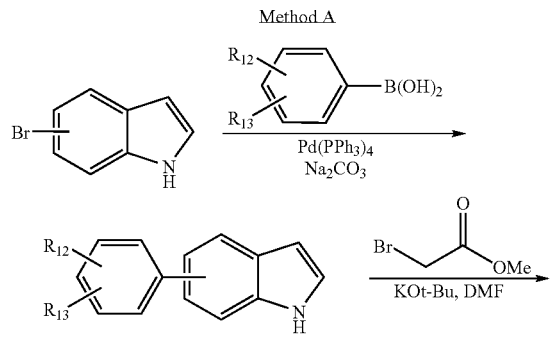

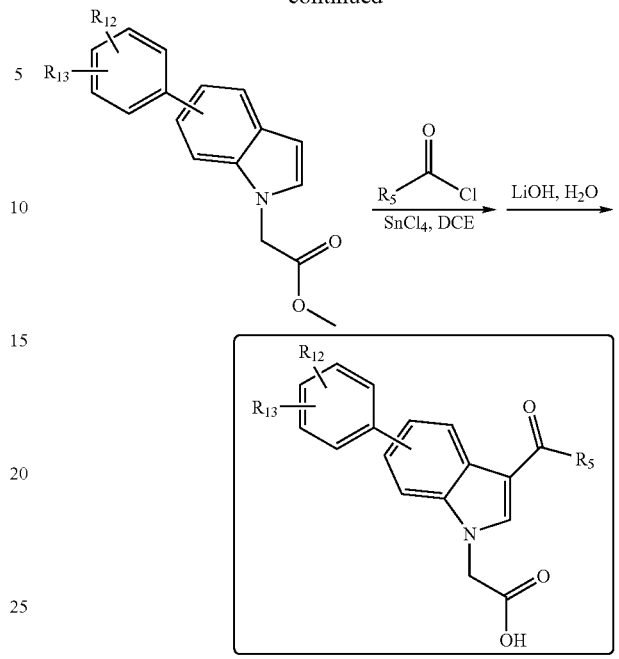

Method B

Indoles containing alkyl, alkenyl and alkynyl substituents may also be prepared from indole substituted on the benzene ring with bromide, iodine, or triflate via palladium catalyzed coupling reaction with primary acetylenes. This reaction can be performed using a palladium catalyst, such as Pd(PPh$_3$)$_4$, a base, such as. HN(i-Pr)$_2$ or EtN(i-Pr)$_2$, with or without a copper salt, such as CuI or CuBr, in an inert solvent, such as MeCN or toluene. The resulting alkynylindoles may be reduced to alkenyl- or alkylindoles by catalytic hydrogenation. Indoles substituted with alkyl, cycloalkyl, and benzyl groups can be prepared from the same substituted indoles by a nickel catalyzed coupling reaction. This reaction uses an alkylmagnesium coupling partner, such as $C_6H_{11}CH_2MgCl$, PhCH$_2$MgCl, or PhCMe$_2$CH$_2$MgCl and a nickel catalyst, such as Ni(dppf)Cl$_2$ (dppf=1,1'-bis(diphenylphosphino)ferrocene) to give the corresponding substituted indoles. These indoles can then be further elaborated as described in Method A to give the desired indol-1-yl acetic acids.

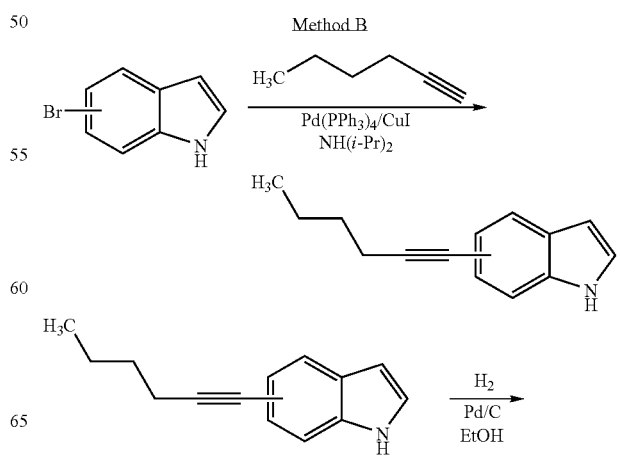

-continued

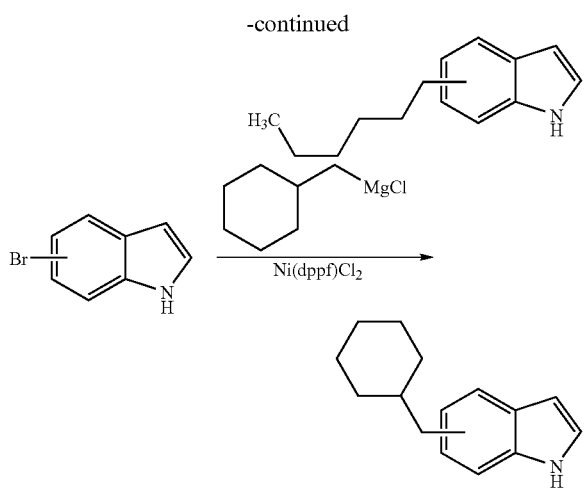

This invention also provides pharmaceutical compositions comprising substituted 1H-indol-1-yl acetic acid derivatives of Formula I as described herein either alone or in combination with excipients (i.e. pharmaceutically acceptable materials with no pharmacological effects and pharmaceutically acceptable carriers). A pharmaceutically or therapeutically effective amount of a compound of this invention refers to an amount of the compound which will sufficiently inhibit the severe protease, inhibitor PAI-1 in a mammal in need thereof to provide sufficient inhibition of PAI-1.

The precise dosage to be employed depends upon several factors including the host, whether in veterinary medicine or human medicine, the nature and severity of the condition being treated, the mode of administration and the particular active substance employed. The compounds may be administered by any conventional route, in particular enterally, preferably orally in the form of tablets or capsules. Administered compounds can be in the free form or pharmaceutically acceptable salt form as appropriate, for use as a pharmaceutical, particularly for use in the prophylactic or curative treatment of atherosclerosis and sequelae (angina pectoris, myocardial infarction, arrhythmias, heart failure, kidney failure, stroke, peripheral arterial occlusion, and related disease states). These measures will slow the rate of progress of the disease state and assist the body in reversing the process direction in a natural manner.

Any suitable carrier known to the art can be used to prepare the pharmaceutical compositions. In such a composition, the carrier may be a solid, liquid or mixture of a solid and a liquid. Solid compositions include powders, tablets and capsules. A solid carrier can be one or more substances which may also act as a flavoring agent, lubricant, solubilizer, suspending agent, binder, or tablet disintegrant. In powders, the carrier is a finely divided solid, which is in admixture with the finely divided active ingredient. In tablets, the active ingredient is mixed with a carrier having the necessary binding properties in suitable proportions and compacted in the shape and size desired. Suitable solid carriers are magnesium carbonate, magnesium stearate, talc, sugar, lactose, pectin, dextrin, starch, gelatin, tragacanth, methyl cellulose, hydroxymethyl cellulose, sodium carboxymethyl cellulose, a low melting wax, cocoa butter, and the like. Encapsulating materials may also be employed with the compounds of this invention, and the term "composition" is intended to include the active ingredient in combination with an encapsulating material as a formulation, with or without other carriers. Cachets may also be used in the delivery of the anti-atherosclerotic medicament of this invention.

Sterile liquid compositions include solutions, suspensions, emulsions, syrups and elixirs. The compounds of this invention may be dissolved or suspended in the pharmaceutically acceptable carrier, such as sterile water, sterile organic solvent or a mixture of both. Preferably the liquid carrier is one suitable for parental injection. Where the compounds are sufficiently soluble they can be dissolved directly in normal saline with or without the use of suitable organic solvents, such as propylene glycol or polyethylene glycol. If desired, dispersions of the finely divided compounds can be made-up in aqueous starch or sodium carboxymethyl cellulose solution, or in a suitable oil, such as arachis oil. Liquid pharmaceutical compositions, which are sterile solutions or suspensions, can be utilized by intramuscular, intraperitoneal or subcutaneous injection. In many instances a liquid composition form may be used instead of the preferred solid oral method of administration.

It is preferred to prepare unit dosage forms of the compounds for standard administration regimens. In this way, the composition can be subdivided readily into smaller doses at the physicians direction. For example, unit dosages may be made up in packeted powders, vials or ampoules and preferably in capsule or tablet form. The active compound present in these unit dosage forms of the composition may be present in an amount of from about one gram to about fifteen grams or more, for single or multiple daily administration, according to the particular need of the patient. The daily dose of active compound will vary depending upon the route of administration, the size, age and sex of the patient, the severity of the disease state, and the response to the therapy as traced by blood analysis and the patients recovery rate. By initiating the treatment regimen with a minimal daily dose of about one gram, the blood levels of PAI-1 and the patients symptomatic relief analysis may be used to determine whether a larger dose is indicated. Based upon the data presented below, the projected daily dose for both human and veterinary use will be from about 25 to about 200 milligrams/kilogram per day, and more usually, from about 50 to about 100 milligrams/kilogram per day.

The ability of the compounds of this invention to inhibit plasminogen activator inhibitor-1 was established by the following experimental procedures:

Primary Screen for the PAI-1 Inhibition

Test compounds were dissolved in DMSO at a final concentration of 10 mM, then diluted 100× in physiologic buffer. The inhibitory assay was initiated by the addition of the test compound (1-100 µM final concentration, maximum DMSO concentration of 0.2%) in a pH 6.6 buffer containing 140 nM recombinant human plasminogen activator inhibitor-1 (*Molecular Innovations*, Royal Oak, Mich.). Following a 1 hour incubation at room temperature, 70 nM of recombinant human tissue plasminogen activator (tPA) was added, and the combination of the test compound, PAI-1 and tPA was incubated for an additional 30 minutes. Following the second incubation, Spectrozyme-tPA (*American Diagnostica*, Greenwich, Conn.), a chromogenic substrate for tPA, was added and absorbance was read at 405 nm at 0 and 60 minutes. Relative PAI-1 inhibition was equal to the residual tPA activity in the presence of the test compound and PAI-1. Control treatments included the complete inhibition of tPA by PAI-1 at the molar ratio employed (2:1), and the absence of any effect of the test compound on tPA alone.

Assay for Determining $IC_{50}$ of Inhibition of PAI-1

This assay was based upon the non-SDS dissociable interaction between tPA and active PAI-1. Assay plates were initially coated with human tPA (10 μg/ml). The test compounds were dissolved in DMSO at 10 mM, then diluted with physiologic buffer (pH 7.5) to a final concentration of 1-50 μM. The test compounds were incubated with human PAI-1 (50 ng/ml) for 15 minutes at room temperature. The tPA-coated plate was washed with a solution of 0.05% Tween 20 and 0.1% BSA, then the plate was blocked with a solution of 3% BSA. An aliquot of the test compound/PAI-1 solution was then added to the tPA-coated plate, incubated at room temperature for 1 hour and washed. Active PAI-1 bound to the plate was assessed by adding an aliquot of a 1:1000 dilution of the 33B8 monoclonal antibody against human PAI-1, and the plate was incubated at room temperature for 1 hour (*Molecular Innovations*, Royal Oak, Mich.). The plate was again washed, and a solution of goat anti-mouse IgG-alkaline phosphatase conjugate was added at a 1:50,000 dilution in goat serum. The plate was incubated 30 minutes at room temperature, washed, and a solution of alkaline phosphatase substrate was added. The plate was incubated 45 minutes at room temperature, and color development was determined at $OD_{405nm}$. The quantitation of active PAI-1 bound to tPA at varying concentrations of test compound was used to determine the $IC_{50}$. Results were analyzed using a logarithmic best-fit equation. The assay sensitivity was 5 ng/ml of human PAI-1 as determined from a standard curve ranging from 0-100 ng/ml.

The compounds of the present invention inhibited Plasminogen Activator Inhibitor-1 as summarized in Table I.

TABLE 1

Inhibition of Plasminogen Activator Inhibitor-1 by Examples 1-3

| Example | % Inhibition @ 25 uM |
|---|---|
| 1 | 47 |
| 2 | 45 |
| 3 | 46 |

EXAMPLE 1

[3-(4-chlorobenzoyl)-5-(4-chlorophenyl)-1H-indol-1-yl]acetic acid

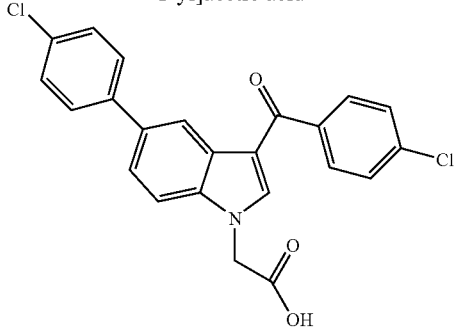

Step 1:

A stirred slurry of 6.35 g (60 mmol) $K_2CO_3$, 2.94 g (15 mmol) 5-bromoindole, 2.50 g (16 mmol) 4-chlorophenylboronic acid, and 0.48 g (0.42 mmol) tetrakistriphenylphosphine palladium was heated to reflux for 2½ hours. The reaction mixture was allowed to cool and was then poured into 200 ml water and extracted with EtOAc. The organic layer was separated, dried over $MgSO_4$, and concentrated. The residue was chromatographed on silica to afford 1.39 g 5-(4-chlorophenyl)indole as a white solid.

Step 2:

To a solution of 0.68 g (3.0 mmol) 5-(4-chlorophenyl) indole in 20 ml anhydrous DMF was added 3.1 ml 1.0 M solution of KOt-Bu in THF. The solution was stirred at room temperature for 15 min and then 0.29 ml (3.1 mmol) methyl bromoacetate was added. The solution was stirred at room temperature overnight. The solution was concentrated under vacuum and the residue was dissolved in a minimal amount of EtOAc. This solution was washed once with water and the organic phase was decanted from the aqueous phase with a pipet and loaded directly on a column of silica where it was chromatographed using 15-25% EtOAc-hexane. This afforded 0.485 g [5-(4-chloro-phenyl)-indol-1-yl]-acetic acid methyl ester as a solid.

Step 3:

To a solution of 0.485 g (1.61 mmol) product from Step 2 and 0.24 ml (1.9 mmol) 4-chlorobenzoyl chloride in 10 ml dichloroethane, cooled to 0° C. in ice, was added 1.9 ml 1.0 M solution $SnCl_4$ in DCM. The ice bath was removed and the reaction allowed to stir at room temperature overnight. The solution was poured into saturated aqueous $NaHCO_3$ with stirring and the solution was extracted with EtOAc. The organic phase was dried over $MgSO_4$ and concentrated. The residue was chromatographed on silica using 20-40% EtOAc-hexane to afford a solid which was triturated from diethyl ether to afford 0.30 g [3-(4-chloro-benzoyl)-5-(4-chloro-phenyl)-indol-1-yl]-acetic acid methyl ester as colorless crystals.

Step 4:

To a solution of 0.30 g (0.68 mmol) product from Step 3 in 5 ml THF was added a solution of 0.11 g (2.72 mmol) lithium hydroxide hydrate in 5 ml water. The solution was stirred at room temperature overnight, acidified with 4 ml 1 N aqueous HCL, diluted with water, and extracted once each with dichloromethane and EtOAc. The combined organic extracts were concentrated and the residue was purified by RP-HPLC to afford 0.106 g Example 1: mp 255-257° C.; $^1$H NMR (DMSO-$d_6$, 300 MHz) δ 5.20 (s, 2H), 7.54 (d, J=8.4 Hz, 2H), 7.58-7.71 (m, 4H), 7.72 (d, J=8.7 Hz, 2H) 7.82 (d, J=8.4 Hz, 2H), 8.16 (s, 1H), 8.52 (s, 1H); MS: m/z (ESI) 422 (M−H); Anal. calcd for ($C_{23}H_{15}Cl_2NO_3$) C, H, N.

The compounds of Examples 2 and 3 were prepared by the method used to prepare the compound of Example I, using 5-bromoindole, 4-methylbenzeneboronic acid, benzo[b]thiophene-2-carbonyl chloride, and 4-chlorobenzoyl chloride and purified by semi-preparative RP-HPLC[1].

EXAMPLE 2

[3-(Benzo[b]thiophene-2-carbonyl)-5-(4-methyl phenyl)-1H-indol-1-yl]-acetic acid

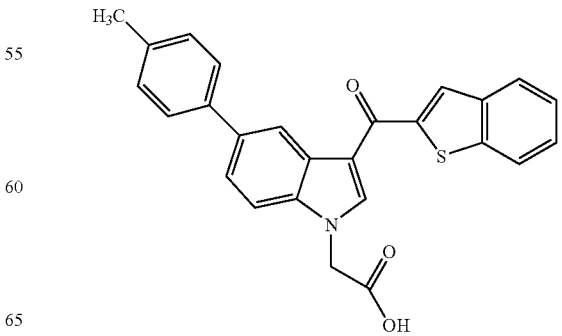

MS: m/z (ESI) 426 (M+H); LCMS² retention time: 2.15 min.

EXAMPLE 3

[3-(4-chlorobenzoyl)-5-(4-methylphenyl)-1H-indol-1-yl]-acetic acid

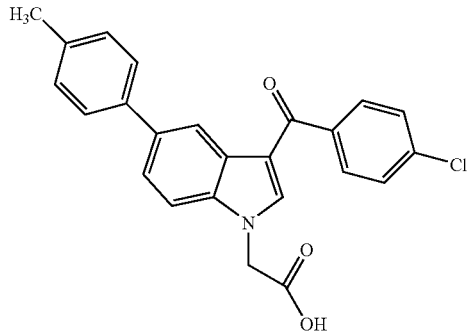

MS: m/z (ESI) 426 (M+H); LCMS² retention time: 1.85 min.

Notes:
1. Semi-Preparative RP-HPLC Conditions:
Gilson Semi-Preparative HPLC system with Unipoint Software
Column: Phenomenex C18 Luna 21.6 mm×60 mm, 5 µM;
Solvent A: Water (0.02% TFA buffer); Solvent B: Acetonitrile (0.02% TFA buffer); Solvent Gradient: Time 0: 5% B; 2.5 min: 5% B; 7 min: 95% B; Hold 95% B 5 min.
Flow Rate: 22.5 mL/min
The product peak was collected based on UV absorption and concentrated.
2. Analytical LCMS Conditions:
Hewlett Packard 1100 MSD with ChemStation Software
Column: YMC ODS-AM 2.0 mm×50 mm 5µ column at 23° C.
Solvent A: Water (0.02% TFA buffer)
Solvent B: Acetonitrile (0.02% TFA buffer)
Gradient: Time 0: 5% B; 0.3 min: 5% B; 3.0 min: 90% B; Hold 95% B 2 min.
Flow rate 1.5 mL/min
Detection: 254 nm DAD; API-ES Scanning Mode Positive 150-700; Fragmentor 70 mV.

What is claimed:

1. Compounds of formula (I):

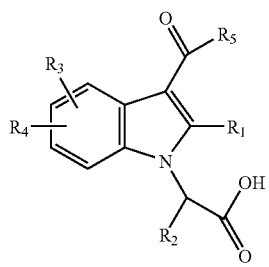

wherein:
$R_1$ is hydrogen, $C_2$-$C_6$ alkyl, $C_3$-$C_6$ cycloalkyl, —$CH_2$—$C_3$-$C_6$ cycloalkyl, or $C_1$-$C_3$ perfluoroalkyl, wherein the alkyl and cycloalkyl groups may be optionally substituted with halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, —$CH_2$—$C_3$-$C_6$ cycloalkyl, phenyl, benzyl, or $CH_2$-naphthyl, wherein the alkyl group and the rings of the cycloalkyl, phenyl, benzyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —$CO_2R_6$, —C(O)$NH_2$, —S(O)$_2CH_3$, —OH, —$NH_2$, or —$NO_2$;

$R_3$ is hydrogen, halogen, $C_1$-$C_6$ alkyl, $C_1$-$C_3$ perfluoroalkyl, $C_1$-$C_6$ alkoxy, $C_3$-$C_6$ cycloalkyl, —$CH_2$—$C_3$-$C_6$ cycloalkyl, —$NH_2$, or —$NO_2$;

$R_4$ is $C_3$-$C_6$ cycloalkyl, —$CH_2$—$C_3$-$C_6$ cycloalkyl, phenyl, or naphthyl, wherein the rings of the cycloalkyl, phenyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, $CH_2CO_2H$, —C(O)$CH_3$, —C(O)$OR_6$, —C(O)$NH_2$, —S(O)$_2CH_3$, —OH, —$NH_2$, or —$NO_2$;

$R_5$ is thienyl, $CH_2$-thienyl, furanyl, $CH_2$-furanyl, oxazoyl, $CH_2$-oxazoyl, benzo[b]furan-2-yl, benzo[b]thien-2-yl, or benzo[1,3]dioxol-5-yl, the rings of the thienyl, furanyl, oxazoyl, benzofuranyl, and benzothienyl, groups may be optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, phenoxy, —$OCHF_2$, —CN, —COOH, —$CH_2CO_2H$, —C(O)$CH_3$, —$CO_2R_6$, —C(O)$NH_2$, —S(O)$_2CH_3$, —OH, —$NH_2$, or —$NO_2$, wherein the phenoxy group may be optionally substituted by from 1 to 3 groups selected from halogen, $C_1$-$C_3$ alkyl, or $C_1$-$C_3$ perfluoroalkyl; and $R_6$ is $C_1$-$C_6$ alkyl, $C_3$-$C_6$ cycloalkyl, —$CH_2$—$C_3$-$C_6$ cycloalkyl, or benzyl; or a pharmaceutically acceptable salt or ester form thereof.

2. The compound of claim 1 wherein $R_1$-$R_3$ and $R_5$-$R_6$ are as defined in claim 1, and $R_4$ is phenyl, or naphthyl, wherein the rings of the phenyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —C(O)$OR_6$, —C(O)$NH_2$, —S(O)$_2CH_3$, —OH, —$NH_2$, or —$NO_2$.

3. The compound of claim 1 which is [3-(Benzo[b]thiophene-2-carbonyl)-5-(4-methylphenyl)-1H-indol-1-yl]-acetic acid, or a pharmaceutically acceptable salt or ester form thereof.

4. A method of inhibiting in a mammal plasminogen activator inhibitor type I, comprising administering to a mammal in need thereof a therapeutically effective amount of a compound of formula (I)

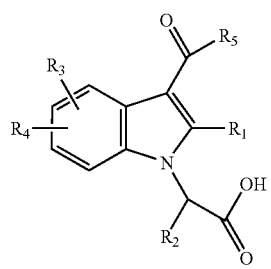

wherein:

$R_1$ is hydrogen, $C_2$-$C_6$ alkyl, $C_3$-$C_6$ cycloalkyl, —$CH_2$—$C_3$-$C_6$ cycloalkyl, or $C_1$-$C_3$ perfluoroalkyl, wherein the alkyl and cycloalkyl groups may be optionally substituted with halogen, —CN, $C_1$-$C_6$ alkoxy, —OH, —$NH_2$, or —$NO_2$;

$R_2$ is hydrogen, $C_1$-$C_8$ alkyl, $C_3$-$C_6$ cycloalkyl, —$CH_2$—$C_3$-$C_6$ cycloalkyl, phenyl, benzyl, or $CH_2$-naphthyl, wherein the alkyl group and the rings of the cycloalkyl, phenyl, benzyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, —$CH_2CO_2H$, —C(O)$CH_3$, —$CO_2R_6$, —C(O)$NH_2$, —S(O)$_2CH_3$, —OH, —$NH_2$, or —$NO_2$;

$R_3$ is hydrogen, halogen, $C_1$-$C_6$ alkyl, $C_1$-$C_3$ perfluoroalkyl, $C_1$-$C_6$ alkoxy, $C_3$-$C_6$ cycloalkyl, —$CH_2$—$C_3$-$C_6$ cycloalkyl, —$NH_2$, or —$NO_2$;

$R_4$ is $C_3$-$C_6$ cycloalkyl, —$CH_2$—$C_3$-$C_6$ cycloalkyl, phenyl, or naphthyl, wherein the rings of the cycloalkyl, phenyl, and napthyl groups may be optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, $CH_2CO_2H$, —C(O)$CH_3$, —C(O)$OR_6$, —C(O)$NH_2$, —S(O)$_2CH_3$, —OH, —$NH_2$, or —$NO_2$;

$R_5$ is thienyl, $CH_2$-thienyl, furanyl, $CH_2$-furanyl, oxazoyl, $CH_2$-oxazoyl, benzo[b]furan-2-yl, benzo[b]thien-2-yl, or benzo[1,3]dioxol-5-yl rings of the thienyl, furanyl, oxazoyl, benzofuranyl, and benzothienyl groups may be optionally substituted by from 1 to 3 groups selected from halogen, $C_1$-$C_3$ alkyl, $C_3$-$C_6$ cycloalkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, phenoxy, —$OOHF_2$, —CN, —COOH, —$CH_2CO_2H$, —C(O)$CH_3$, —$CO_2R_6$, —C(O)$NH_2$, —S(O)$_2CH_3$, —OH, —$NH_2$, or —$NO_2$, wherein the phenoxy group may be optionally substituted by from 1 to 3 groups selected from halogen, $C_1$-$C_3$ alkyl, or $C_1$-$C_3$ perfluoroalkyl; and $R_6$ is $C_1$-$C_6$ alkyl, $C_3$-$C_6$ cycloalkyl, —$CH_2$—$C_3$-$C_6$ cycloalkyl, or benzyl; or a pharmaceutically acceptable salt or ester form thereof.

5. A pharmaceutical composition comprising a compound of claim 1 and a pharmaceutical carrier.

6. A method for treatment of thrombosis or fibrinolytic impairment in a mammal, the method comprising administering to a mammal in need thereof a pharmaceutically effective amount of a compound of claim 1.

7. A method of claim 6 wherein the thrombosis or fibrinolytic impairment is associated with formation of atherosclerotic plaques, venous and arterial thrombosis, myocardial ischemia, atrial fibrillation, deep vein thrombosis, coagulation syndromes, pulmonary fibrosis, cerebral thrombosis, thromboembolic complications of surgery or peripheral arterial occlusion.

8. A method for the treatment of peripheral arterial disease in a mammal, comprising administering to a mammal in need thereof a pharmaceutically effective amount of a compound of claim 1.

9. A method for the treatment of stroke associated with or resulting from atrial fibrillation in a mammal, comprising administering to a mammal in need thereof a pharmaceutically effective amount of a compound of claim 1.

10. A method for the treatment of deep vein thrombosis in a mammal, comprising administering to a mammal in need thereof a pharmaceutically effective amount of a compound of claim 1.

11. A method for the treatment of myocardial ischemia in a mammal, comprising administering to a mammal in need thereof a pharmaceutically effective amount of a compound of claim 1.

12. A method for the treatment of the formation of atherosclerotic plaques in a mammal, comprising administering to a mammal in need thereof a pharmaceutically effective amount of a compound of claim 1.

13. A method for the treatment of chronic obstructive pulmonary disease in a mammal, comprising administering to a mammal in need thereof a pharmaceutically effective amount of a compound of claim 1.

14. A method for the treatment of renal fibrosis in a mammal, comprising administering to a mammal in need thereof a pharmaceutically effective amount of a compound of claim 1.

15. The compound of claim 2, wherein $R_1$ is H.

16. The compound of claim 2, wherein $R_2$ is H.

17. The compound of claim 2, wherein $R_3$ is H.

18. The compound of claim 2, wherein $R_4$ is phenyl, optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, $CH_2CO_2H$, —C(O)$CH_3$, —C(O)$OR_6$, —C(O)$NH_2$, —S(O)$_2CH_3$, —OH, —$NH_2$, or —$NO_2$.

19. The compound of claim 2, wherein $R_1$, $R_2$, $R_3$ are each H and $R_4$ is phenyl, optionally substituted by from 1 to 3 groups selected from halogen, $C_1$-$C_3$ alkyl, $C_1$-$C_3$ perfluoroalkyl, —O—$C_1$-$C_3$ perfluoroalkyl, —S—$C_1$-$C_3$ perfluoroalkyl, $C_1$-$C_3$ alkoxy, —$OCHF_2$, —CN, —COOH, $CH_2CO_2H$, —C(O)$CH_3$, —C(O)$OR_6$, —C(O)$NH_2$, —S(O)$_2CH_3$, —OH, —$NH_2$, or —$NO_2$.

* * * * *